(12) United States Patent
Ebata

(10) Patent No.: US 11,490,879 B2
(45) Date of Patent: Nov. 8, 2022

(54) ACOUSTIC WAVE DIAGNOSTIC APPARATUS AND CONTROL METHOD OF ACOUSTIC WAVE DIAGNOSTIC APPARATUS

(71) Applicant: FUJIFILM Corporation, Tokyo (JP)

(72) Inventor: Tetsurou Ebata, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 42 days.

(21) Appl. No.: 16/933,808

(22) Filed: Jul. 20, 2020

(65) Prior Publication Data

US 2020/0345331 A1 Nov. 5, 2020

Related U.S. Application Data

(63) Continuation of application No. PCT/JP2019/005753, filed on Feb. 18, 2019.

(30) Foreign Application Priority Data

Mar. 16, 2018 (JP) .............................. JP2018-050048

(51) Int. Cl.
*A61B 8/00* (2006.01)
*A61B 8/08* (2006.01)
*G06F 3/14* (2006.01)

(52) U.S. Cl.
CPC ................ *A61B 8/54* (2013.01); *A61B 8/085* (2013.01); *A61B 8/463* (2013.01); *A61B 8/469* (2013.01); *G06F 3/14* (2013.01)

(58) Field of Classification Search
CPC ........... A61B 8/54; A61B 8/085; A61B 8/463; A61B 8/469; A61B 5/0095; A61B 5/1075;
(Continued)

(56) References Cited

U.S. PATENT DOCUMENTS

2004/0207661 A1* 10/2004 Akaki ................... A61B 8/463
715/764
2008/0097209 A1 4/2008 Lee et al.
(Continued)

FOREIGN PATENT DOCUMENTS

EP 3 028 638 A1 6/2016
JP 2008-100073 A 5/2008
(Continued)

OTHER PUBLICATIONS

International Search Report issued in PCT/JP2019/005753; dated Mar. 12, 2019.
(Continued)

*Primary Examiner* — Joseph M Santos Rodriguez
*Assistant Examiner* — Kaitlyn E Sebastian
(74) *Attorney, Agent, or Firm* — Studebaker & Brackett PC

(57) ABSTRACT

An acoustic wave diagnostic apparatus 1 includes a display unit 7; an operation unit 16; a measurement item designation acceptance unit 13 that accepts designation of a measurement item; a detection and measurement algorithm setting unit 9 that sets a detection and measurement algorithm according to a measurement item; a position designation acceptance unit 14 that accepts designation of a measurement position; a measurement unit 8 that detects a measurement target and sets a caliper on the measurement target to perform measurement on the basis of the measurement position and the detection and measurement algorithm; a contour detection unit 10 that detects a contour of the measurement target; a caliper movable range limit unit 11 that limits a movable range of the caliper on the contour of the measurement target according to a modification request of the caliper; and a modification acceptance unit 15 that accepts a modification of the caliper through the operation
(Continued)

unit 16, in which the measurement unit 8 performs measurement using the modified caliper.

20 Claims, 12 Drawing Sheets

(58) Field of Classification Search
CPC ..... A61B 5/1076; A61B 5/743; A61B 5/7435; A61B 8/5223; A61B 8/467; G06F 3/14; G16H 30/20; G16H 30/40; G16H 40/63
See application file for complete search history.

(56) References Cited

U.S. PATENT DOCUMENTS

| | | | |
|---|---|---|---|
| 2014/0121524 A1 | 5/2014 | Chiang et al. | |
| 2016/0085328 A1 | 3/2016 | Lee et al. | |
| 2017/0090571 A1* | 3/2017 | Bjaerum | A61B 8/4254 |
| 2017/0090675 A1* | 3/2017 | Lee | A61B 8/469 |
| 2017/0124700 A1* | 5/2017 | Sarojam | A61B 8/46 |
| 2018/0242952 A1* | 8/2018 | Satoh | A61B 8/0841 |

FOREIGN PATENT DOCUMENTS

| | | | |
|---|---|---|---|
| JP | 2010-240198 A | | 10/2010 |
| JP | 2012019824 A | * | 2/2012 |
| JP | 2017-109074 A | | 6/2017 |
| WO | 2009/037616 A2 | | 3/2009 |
| WO | 2012/014691 A1 | | 2/2012 |

OTHER PUBLICATIONS

International Preliminary Report on Patentability and Written Opinion issued in PCT/JP2019/005753; dated Sep. 22, 2020.
Gabriella Csurka et al.; "Visual Categorization with Bags of Keypoints"; Proc. Of ECCV Workshop on Statistical Learning in Computer Vision; 2004; pp. 59-74.
Alex Krizhevsky et al.; "ImageNet Classification with Deep Convolutional Neural Networks"; Advances in Neural Information Processing Systems 25; 2012; pp. 1106-1114.
The extended European search report issued by the European Patent Office dated Mar. 19, 2021, which corresponds to European Patent Application No. 19767456.7-1126 and is related to U.S. Appl. No. 16/933,808.

* cited by examiner

ACOUSTIC WAVE DIAGNOSTIC APPARATUS AND CONTROL METHOD OF ACOUSTIC WAVE DIAGNOSTIC APPARATUS

CROSS-REFERENCE TO RELATED APPLICATIONS

This application is a Continuation of PCT International Application No. PCT/JP2019/005753 filed on Feb. 18, 2019, which claims priority under 35 U.S.C. § 119(a) to Japanese Patent Application No. 2018-050048 filed on Mar. 16, 2018. The above application is hereby expressly incorporated by reference, in its entirety, into the present application.

BACKGROUND OF THE INVENTION

1. Field of the Invention

The present invention relates to an acoustic wave diagnostic apparatus and a control method of the acoustic wave diagnostic apparatus, and in particular, to an acoustic wave diagnostic apparatus and a control method of the acoustic wave diagnostic apparatus which perform detection and measurement of a measurement target on an acoustic wave image.

2. Description of the Related Art

In recent years, medical acoustic wave diagnostic apparatuses generally have a measurement function of measuring the length, size, area, and the like of various organs, lesions, and the like included in an acquired acoustic wave image. In order to measure a measurement target, usually, a user operates a caliper, that is, a cursor using an input device for inputting coordinates, such as a trackpad, a trackball, and a mouse, to set a measurement point, a region of interest, or the like on a display image. As described above, in a case where a manual operation is performed by the user, there is an influence due to the user's experience, skill level, and the like, and therefore, various attempts have been made to automate the operation.

For example, JP2010-240198A discloses an ultrasound diagnostic apparatus that automatically sets optimal image mode, image quality setting, measurement mode, and measurement item for a measurement target in a case where a body mark for the measurement target is selected by a user through an operation unit. In JP2010-240198A, for an ultrasound image, a measurement target is measured based on the position, number, and order of measurement points input from the user through the operation unit, and a measurement result thereof is displayed on a display unit.

SUMMARY OF THE INVENTION

As described above, in the ultrasound diagnostic apparatus disclosed in JP2010-240198A, since it is necessary to manually designate a measurement point and a designation point through the operation unit, the measurement requires time and effort. Thus, it is desired that in a case where a user simply designates an approximate position on an ultrasound image in which a measurement target is present, measurement is performed by automatically searching a surrounding area of the position and detecting the measurement target.

However, the position where the caliper is disposed and the measurement rule may differ depending on the users, and in some cases, the automatically set position of the caliper may be modified manually. Thus, in a case where the user tries to manually move the caliper to the position considered to be correct by switching the caliper setting to a manual mode, it takes a lot of time and effort for the operation, especially in case of a small terminal, more precise operation is required, and therefore there is a problem in that the burden on the user and the operation time are increased.

The invention has been made in order to solve such a problem in the related art, and an object of the invention is to provide an acoustic wave diagnostic apparatus, and a control method of the acoustic wave diagnostic apparatus which are capable of easily and accurately modifying manually an automatically set position of a caliper.

In order to achieve the object, an acoustic wave diagnostic apparatus according to an aspect of the invention comprises a display unit that displays an acquired acoustic wave image; an operation unit that is used for a user to perform an input operation; a measurement item designation acceptance unit that accepts designation of a measurement item relating to a measurement target through the operation unit; a detection and measurement algorithm setting unit that sets a detection and measurement algorithm on the basis of the measurement item accepted by the measurement item designation acceptance unit; a position designation acceptance unit that accepts designation of a position of the measurement target on the acoustic wave image displayed on the display unit, through the operation unit; a measurement unit that detects the measurement target and sets a caliper on the detected measurement target to perform measurement on the basis of the position of the measurement target accepted by the position designation acceptance unit and the detection and measurement algorithm set by the detection and measurement algorithm setting unit, and causes the display unit to display a measurement result; a contour detection unit that detects a contour of the measurement target on the acoustic wave image; a caliper movable range limit unit that limits a movable range of the caliper to the contour detected by the contour detection unit, according to a modification request of a position of the caliper through the operation unit; and a modification acceptance unit that accepts a modification of the position of the caliper which is performed through the operation unit, in which the measurement unit measures the measurement target on the basis of the modification of the position of the caliper accepted by the modification acceptance unit, and causes the display unit to display a measurement result.

The caliper movable range limit unit may limit the movable range of the caliper such that a measurement line connected to the caliper is moved while facing a predetermined direction.

The caliper movable range limit unit may calculate an approximate straight line of an edge of the measurement target around the caliper, and limit the movable range of the caliper such that a measurement line connected to the caliper is moved while facing a direction perpendicular to the approximate straight line.

The caliper movable range limit unit may calculate two approximate straight lines of edges of the measurement target which are respectively around two calipers positioned on both ends of a measurement line, and limit the movable range of the caliper such that the measurement line is moved while facing a direction perpendicular to an average angle of the two approximate straight lines.

Further, the caliper movable range limit unit may calculate a recommendation degree for the modification of the position of the caliper in each point on the contour, and change a display method of a measurement line connected to the caliper according to the calculated recommendation degree.

More specifically, the caliper movable range limit unit may calculate the recommendation degree according to edge likelihood of the measurement target.

The caliper movable range limit unit may calculate the recommendation degree according to a difference between a length of the measurement line connected to the caliper and a maximum diameter of the contour.

The caliper movable range limit unit may calculate the recommendation degree according to an angle difference between the measurement line connected to the caliper and a principal axis of inertia of the measurement target.

Further, the caliper movable range limit unit may change at least one of a color, thickness, or type of the measurement line according to the recommendation degree.

The caliper movable range limit unit may cancel limiting the movable range of the caliper on the contour, at a position where the calculated recommendation degree is lower than a predetermined reference value.

Further, the caliper movable range limit unit may learn the modification of the position of the caliper by the user, and further limit the movable range of the caliper to a portion on the contour on the basis of a learning result.

The acoustic wave image is preferably an ultrasound image or a photoacoustic image.

A control method of an acoustic wave diagnostic apparatus according to another aspect of the invention comprises displaying an acquired acoustic wave image; accepting designation of a measurement item relating to a measurement target from a user; setting a detection and measurement algorithm on the basis of the accepted measurement item; accepting designation of a position of the measurement target on the displayed acoustic wave image from the user; detecting the measurement target and sets a caliper on the detected measurement target to perform measurement on the basis of the accepted position of the measurement target and the set detection and measurement algorithm, and displaying a measurement result; detecting a contour of the measurement target on the acoustic wave image; limiting a movable range of the caliper to the detected contour, according to a modification request of a position of the caliper from the user; and accepting a modification of the position of the caliper from the user, in which the measurement target is measured on the basis of the modification of the accepted position of the caliper, and a measurement result is displayed.

According to the invention, since the contour detection unit that detects the contour of the measurement target on the acoustic wave image, the caliper movable range limit unit that limits the movable range of the caliper on the contour detected by the contour detection unit according to the modification request of the position of the caliper through the operation unit, and the modification acceptance unit that accepts the modification of the position of the caliper through the operation unit are comprised, and the measurement unit performs measurement on the measurement target on the basis of the modification of the position of the caliper accepted by the modification acceptance unit to cause the display unit to display the measurement result, it is possible to easily and accurately modify manually an automatically set position of a caliper.

DESCRIPTION OF THE PREFERRED EMBODIMENTS

Hereinafter, embodiments of the invention will be described with reference to the accompanying drawings.

Embodiment 1

Figure 1:
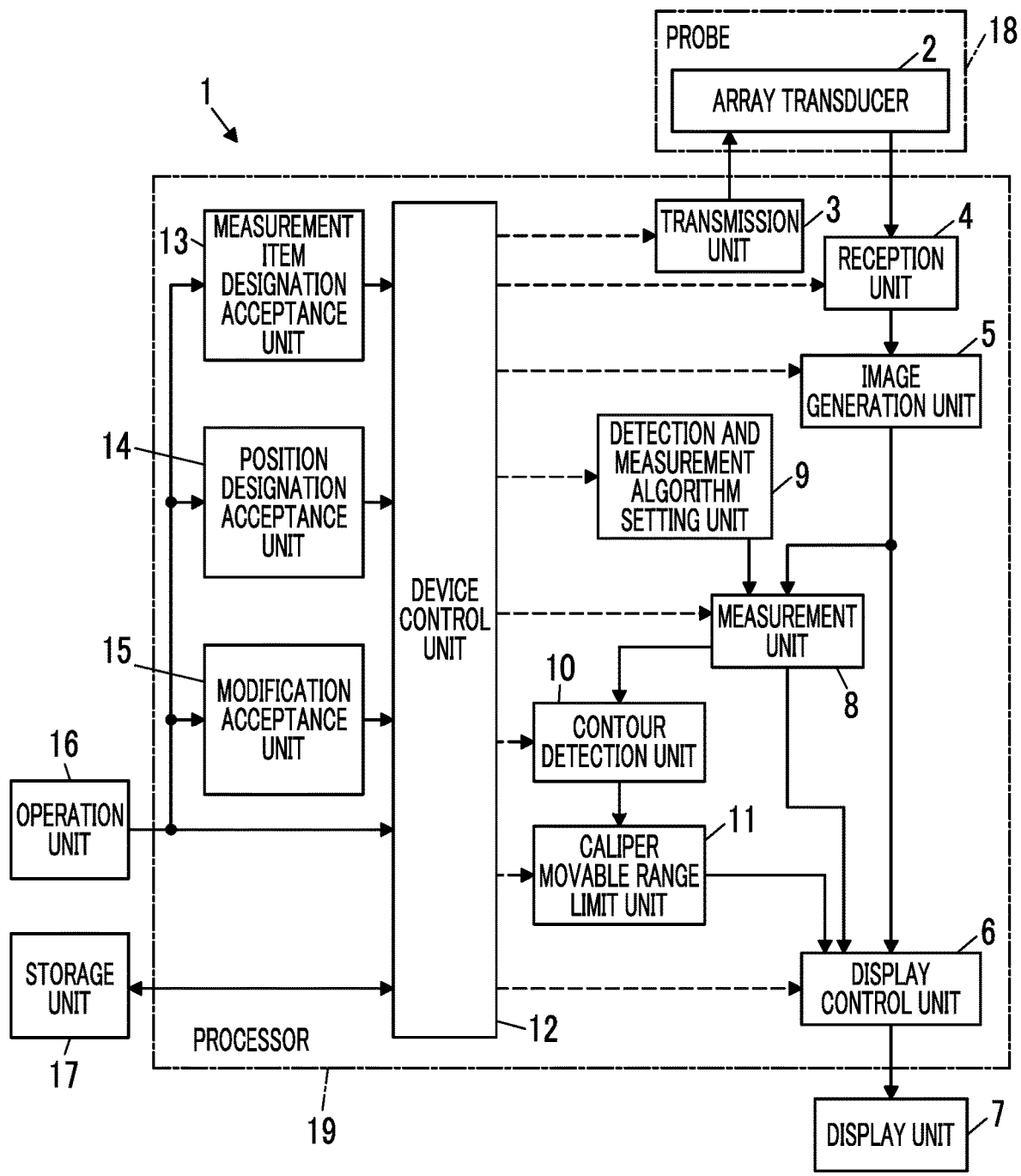
FIG. 1 is a block diagram illustrating a configuration of an ultrasound diagnostic apparatus according to Embodiment 1 of the invention.

FIG. 1 illustrates a configuration of an ultrasound diagnostic apparatus 1 according to Embodiment 1 of the invention. As illustrated in FIG. 1, the ultrasound diagnostic apparatus 1 comprises an array transducer 2, and a transmission unit 3 and a reception unit 4 are connected to the array transducer 2. Further, an image generation unit 5 is connected to the reception unit 4, and a display control unit 6 and a display unit 7 are sequentially connected to the image generation unit 5. Further, a measurement unit 8 is connected to the image generation unit 5, and the measurement unit 8 is connected to the display control unit 6. Further, a detection and measurement algorithm setting unit 9 and a contour detection unit 10 are connected to the measurement unit 8, and a caliper movable range limit unit 11 is connected to the contour detection unit 10. The caliper movable range limit unit 11 is connected to the display control unit 6.

Furthermore, a device control unit 12 is connected to the transmission unit 3, the reception unit 4, the image generation unit 5, the display control unit 6, the measurement unit 8, the detection and measurement algorithm setting unit 9, the contour detection unit 10, and the caliper movable range limit unit 11, and a measurement item designation acceptance unit 13, a position designation acceptance unit 14, a modification acceptance unit 15, an operation unit 16, and a storage unit 17 are connected to the device control unit 12. In addition, the measurement item designation acceptance unit 13, the position designation acceptance unit 14, the modification acceptance unit 15 are connected to the operation unit 16. In addition, the device control unit 12 and the storage unit 17 are connected so as to exchange information bidirectionally.

The array transducer 2 is included in a probe 18. In addition, the transmission unit 3, the reception unit 4, the image generation unit 5, the display control unit 6, the measurement unit 8, the detection and measurement algorithm setting unit 9, the contour detection unit 10, the caliper movable range limit unit 11, the device control unit 12, the measurement item designation acceptance unit 13, the position designation acceptance unit 14, and the modification acceptance unit 15 constitute a processor 19.

The array transducer 2 of the probe 18 illustrated in FIG. 1 has a plurality of ultrasonic transducers arranged in a one-dimensional or two-dimensional manner. According to a drive signal supplied from the transmission unit 3, each of the transducers transmits an ultrasonic wave and receives a reflected wave from a subject to output a reception signal. For example, each transducer is formed by using an element in which electrodes are formed at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission unit 3 of the processor 19 includes, for example, a plurality of pulse generators, and the transmission unit 3 adjusts the amount of delay of each drive signal so that ultrasonic waves transmitted from the plurality of transducers of the array transducer 2 form an ultrasound beam on the basis of a transmission delay pattern selected according to the control signal from the device control unit 12, and supplies the obtained signals to the plurality of transducers. Thus, in a case where a pulsed or continuous-wave voltage is applied to the electrodes of the transducers of the array transducer 2, the piezoelectric body expands and contracts to generate pulsed or continuous-wave ultrasonic waves from each transducer, and an ultrasound beam is formed from the combined wave of these ultrasonic waves.

The transmitted ultrasound beam is reflected by a target, for example, a site of the subject, and propagates toward the array transducer 2 of the probe 18. The ultrasonic waves propagating toward the array transducer 2 in this manner are received by each transducer constituting the array transducer 2. In this case, each transducer constituting the array transducer 2 expands and contracts by receiving the propagating ultrasound echo to generate electrical signals, and outputs the electrical signals to the reception unit 4.

Figure 2:
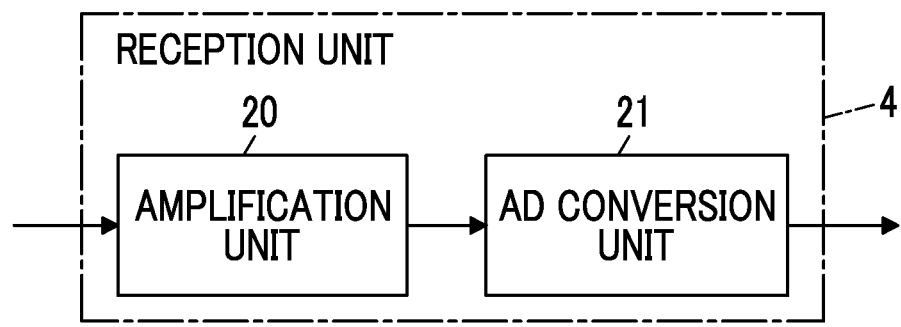
FIG. 2 is a block diagram illustrating an internal configuration of a reception unit in Embodiment 1 of the invention.

The reception unit 4 of the processor 19 processes the reception signals output from the array transducer 2 according to the control signals from the device control unit 12. As illustrated in FIG. 2, the reception unit 4 has a configuration in which an amplification unit 20 and an analog digital (AD) conversion unit 21 are connected in series. The amplification unit 20 amplifies the reception signals input from each element constituting the array transducer 2, and transmits the amplified reception signals to the AD conversion unit 21. The AD conversion unit 21 converts the reception signals transmitted from the amplification unit 20 into digitized data, and sends the data to the image generation unit 5 of the processor 19.

Figure 3:
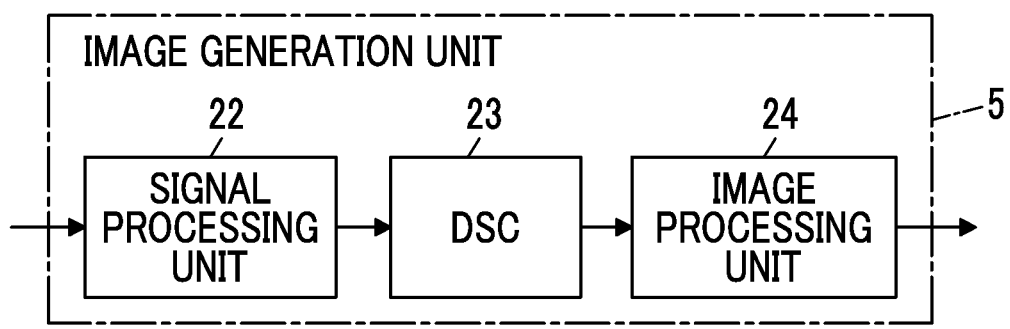
FIG. 3 is a block diagram illustrating an internal configuration of an image generation unit in Embodiment 1 of the invention.

As illustrated in FIG. 3, the image generation unit 5 of the processor 19 has a configuration in which a signal processing unit 22, a digital scan converter (DSC) 23, and an image processing unit 24 are connected in series. The signal processing unit 22 performs reception focusing processing in which addition (phasing addition) is performed by giving delays to respective pieces of element data according to a set sound speed, on the basis of a reception delay pattern selected according to the control signals from the device control unit 12. Through the reception focusing processing, a sound ray signal with narrowed focus of the ultrasound echo is generated. The signal processing unit 22 generates a B mode image signal, which is tomographic image information regarding tissues inside the subject, by performing envelope detection processing after correcting the attenuation of the generated sound ray signal which is caused by the propagation distance according to the depth of the reflection position of the ultrasonic wave. The B mode image signal generated as described above is output to the DSC 23.

The DSC 23 raster-converts the B mode image signal into an image signal according to a normal television signal scanning method. The image processing unit 24 performs various kinds of necessary image processing, such as brightness correction, gradation correction, sharpness correction, and color correction, on the image data obtained in the DSC 23, and then outputs the B mode image signal to the display control unit 6 and the measurement unit 8. The details of the measurement unit 8 will be described below.

The operation unit 16 of the ultrasound diagnostic apparatus 1 is for the user to perform an input operation, and can be configured to comprise a keyboard, a mouse, a trackball, a touchpad, a touch panel, and the like.

The measurement item designation acceptance unit 13 of the processor 19 accepts designation of the measurement item relating to the measurement target from the user through the operation unit 16.

The measurement item relating to the measurement target is an item that can indicate at least one of the measurement target or the measurement content, and the measurement target can include items relating to the name of a target site such as an organ, the name of a lesion such as a tumor, a cyst, bleeding, and abnormalities. In addition, the measurement content can include the length, the area, and the like of the measurement target. Therefore, for example, the measurement item can include any one of only the name of the measurement target, only the name of the lesion, only the item relating to the abnormalities, the name of the measurement target and the measurement content thereof, the name of the lesion and the measurement content thereof, and the item relating to the abnormalities and the measurement content thereof. In a case where the measurement item includes only the measurement target, for example, the measurement content such as whether to measure the length or whether to measure the size is associated with the measurement target designated by the user through the operation unit 16. Specifically, for example, a table in which the measurement target and the measurement content are associated with each other is stored in the storage unit 17 or an external memory (not illustrated), and the measurement content corresponding to the measurement target is selected on the basis of the table.

The position designation acceptance unit 14 of the processor 19 accepts designation of the position of the measurement target on the ultrasound image displayed on the display unit 7, from the user through the operation unit 16.

The detection and measurement algorithm setting unit 9 of the processor 19 sets an algorithm for detecting the measurement target and an algorithm for measuring the measurement target on the basis of the measurement item that the measurement item designation acceptance unit 13 has accepted from the user through the operation unit 16. Generally, the algorithm for detecting the measurement target on the image differs depending on the kind of the measurement target such as organs and lesions. In addition, the algorithm for measuring the measurement target on the image differs depending on the measurement content such as measuring of the length and measuring of the area of the measurement target. The detection and measurement algorithm setting unit 9 stores a table in which algorithms corresponding to respective measurement targets and algorithms corresponding to respective measurement contents are associated with each other, and sets a detection and measurement algorithm with reference to the table in which the algorithms are associated in a case where the measurement item designation acceptance unit 13 accepts the measurement item from the user through the operation unit 16.

As the detection and measurement algorithm, a well-known algorithm that is generally used can be used. Here, the algorithm determines a calculation unit for achieving the purpose such as detection and measurement, and for example, the algorithm is implemented as a software program in an apparatus and is executed by a central processing unit (CPU).

For example, for the algorithm for detecting the measurement target, there is a method of storing typical pattern data in advance as a template, calculating a similarity for the pattern data while searching an image with a template, and considering that a measurement target is present at a location where the similarity is equal to or greater than a threshold value and is the maximum. For the calculation of the similarity, in addition to simple template matching, for example, a machine learning method described in Csurka et al.: Visual Categorization with Bags of Keypoints, Proc. of ECCV Workshop on Statistical Learning in Computer Vision, pp. 59-74 (2004) or a general image recognition method using deep learning described in Krizhevsk et al.: ImageNet Classification with Deep Convolutional Neural Networks, Advances in Neural Information Processing Systems 25, pp. 1106-1114 (2012) can be used.

In a case where the position designation acceptance unit 14 has accepted the designation of the position of the measurement target from the user through the operation unit 16, the measurement unit 8 of the processor 19 detects the measurement target and performs measurement on the detected measurement target on the basis of the accepted position and the detection and measurement algorithm set by the detection and measurement algorithm setting unit 9 to cause the display unit 7 to display the measurement result including the measurement point. Here, in case of detecting the measurement target, the measurement unit 8 detects the measurement target by performing scanning in the scan range set on the ultrasound image on the basis of the detection and measurement algorithm. In addition, in case of performing measurement on the measurement target, the measurement unit 8 disposes the caliper for performing measurement of the measurement target on the ultrasound image on the basis of the detection and measurement algorithm, and measures the measurement target on the basis of the disposed caliper.

The modification acceptance unit 15 of the processor 19 accepts a modification of the position of the caliper disposed on the ultrasound image by the measurement unit 8. Here, the position of the caliper is modified by the user through the operation unit 16.

The contour detection unit 10 of the processor 19 performs an image analysis on the ultrasound image, and detects the contour of the measurement target detected by the measurement unit 8. In this case, for example, the contour detection unit 10 can extract the contour of the measurement target by using a general image recognition method and a machine learning method using deep learning.

In a case where the position of the caliper disposed on the ultrasound image is modified by the user through the operation unit 16, the caliper movable range limit unit 11 of the processor 19 limits the movable range of the caliper on the contour detected by the contour detection unit 10.

The device control unit 12 of the processor 19 controls each unit of the ultrasound diagnostic apparatus 1 on the basis of the program stored in advance in the storage unit 17 or the like and the user's operation through the operation unit 16.

The display control unit 6 of the processor 19 performs predetermined processing on a B mode image generated by the image generation unit 5, the measurement result such as the caliper calculated by the measurement unit 8, the movable range of the caliper limited by the caliper movable range limit unit 11, and the like to cause the display unit 7 to display the B mode image, the measurement result such as the caliper, the movable range of the caliper, and the like under the control of the device control unit 12.

The display unit 7 of the ultrasound diagnostic apparatus 1 displays an image or the like under the control of the display control unit 6, and includes, for example, a display device such as a liquid crystal display (LCD).

The storage unit 17 stores an operation program and the like of the ultrasound diagnostic apparatus 1, and recording media, such as a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), or a server can be used.

The processor 19 having the transmission unit 3, the reception unit 4, the image generation unit 5, the display control unit 6, the measurement unit 8, the detection and measurement algorithm setting unit 9, the contour detection unit 10, the caliper movable range limit unit 11, the device control unit 12, the measurement item designation acceptance unit 13, the position designation acceptance unit 14, and the modification acceptance unit 15 is configured by a CPU and a control program causing the CPU to execute various kinds of processing, but may be configured by a digital circuit. In addition, the transmission unit 3, the reception unit 4, the image generation unit 5, the display control unit 6, the measurement unit 8, the detection and measurement algorithm setting unit 9, the contour detection unit 10, the caliper movable range limit unit 11, the device control unit 12, the measurement item designation acceptance unit 13, the position designation acceptance unit 14, and the modification acceptance unit 15 can also be configured by being integrated partially or entirely into one CPU.

Figure 4:
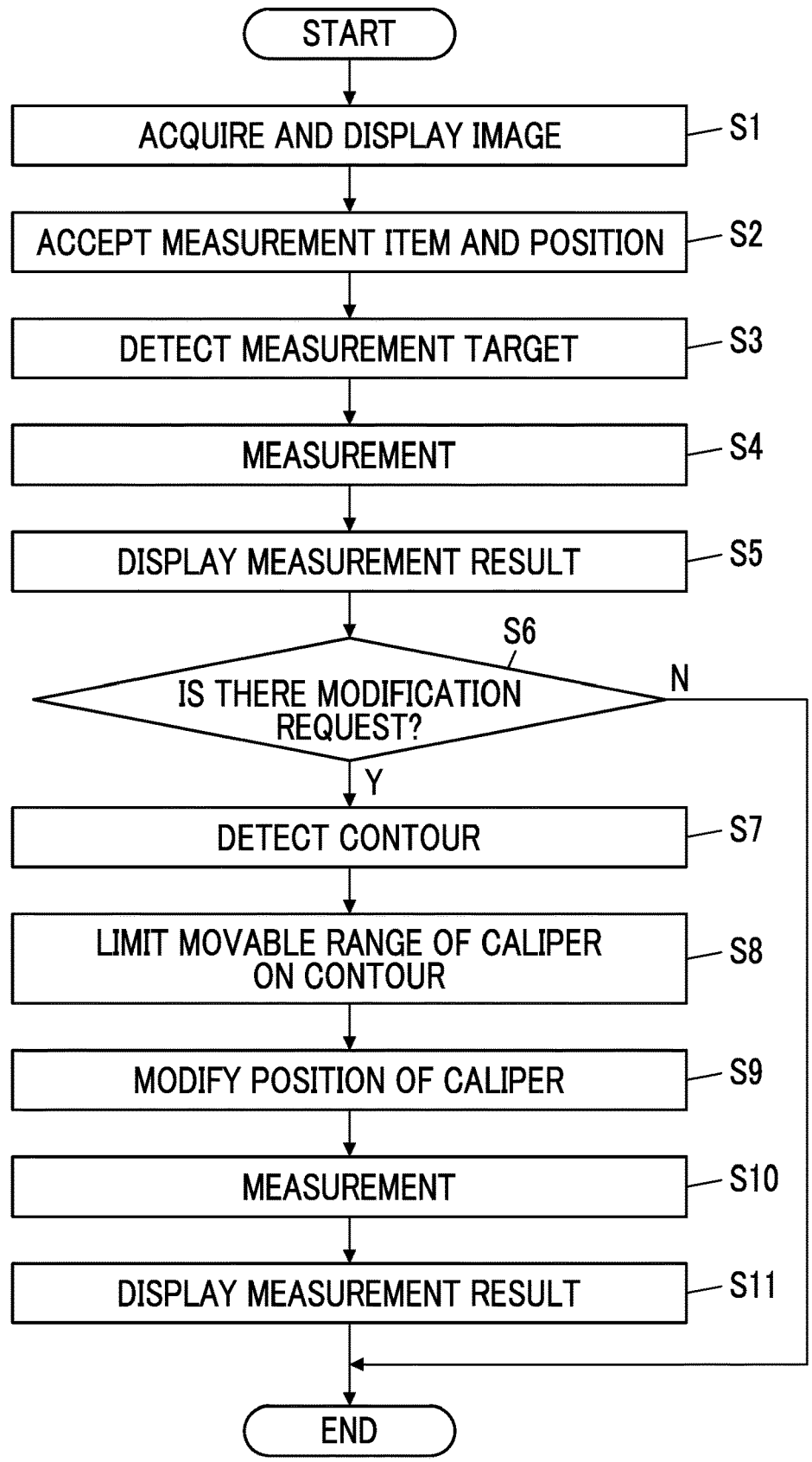
FIG. 4 is a flowchart illustrating an operation of the ultrasound diagnostic apparatus according to Embodiment 1 of the invention.

Next, the measurement operation of the ultrasound diagnostic apparatus 1 according to Embodiment 1 will be described with reference to the flowchart illustrated in FIG. 4.

First, in step S1, an ultrasound image is acquired, and the acquired ultrasound image is displayed on the display unit 7. As the ultrasound image, an image captured on the spot using the probe 18 can be used. Further, the past ultrasound image stored in an image memory (not illustrated) or the like can be used.

Figure 5:
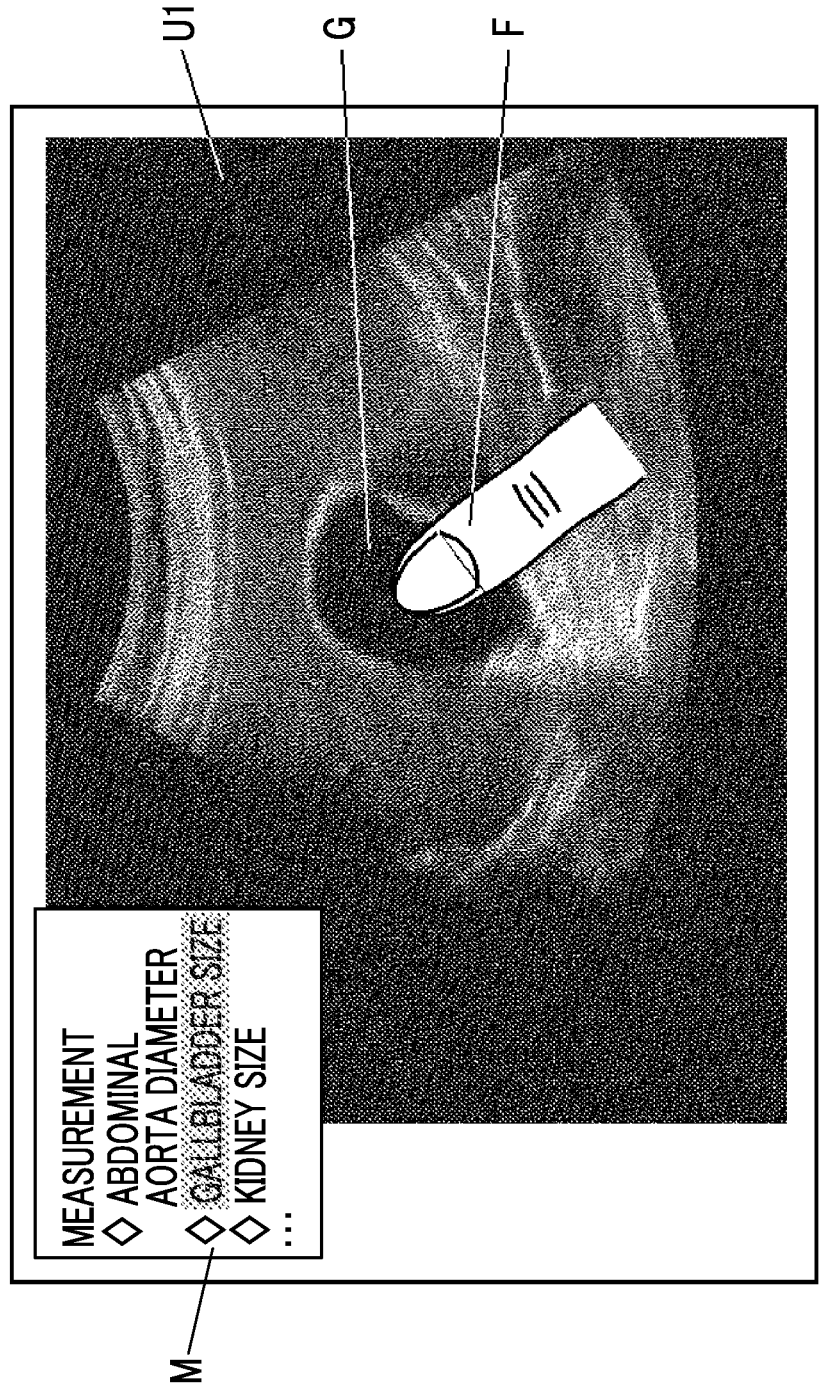
FIG. 5 is a schematic diagram illustrating an aspect in which a user designates a measurement item and a measurement position.

Next, in step S2, the measurement item and the measurement position on the ultrasound image designated from the user through the operation unit 16 are respectively accepted by the measurement item designation acceptance unit 13 and the position designation acceptance unit 14. Here, in a case where the user designates the measurement item, for example, as illustrated in FIG. 5, a list M of the measurement items is displayed on the display unit 7 so that the user can select one of the plurality of measurement items displayed in the list M through the operation unit 16. In the example illustrated in FIG. 5, the gallbladder size is selected as the measurement item. The measurement item designation acceptance unit 13 accepts the measurement item designated by the user in this manner. In a case where the measurement item is accepted, a detection and measurement algorithm according to the measurement item is set by the detection and measurement algorithm setting unit 9.

Further, the user designates one point in a region representing the measurement target in case of designating the measurement position on the ultrasound image. For example, in a case where the display unit 7 is a display with a touch panel and the operation unit 16 is configured by the touch panel of the display unit 7, as illustrated in FIG. 5, the user can designate the measurement position by touching one point in a region representing a gallbladder G on the ultrasound image. The position designation acceptance unit 14 accepts the measurement position designated by the user in this manner.

In step S3, the measurement unit 8 sets a scan range on the ultrasound image and detects the measurement target by performing scanning in the scan range on the basis of the detection and measurement algorithm set by the detection and measurement algorithm setting unit 9.

Figure 6:
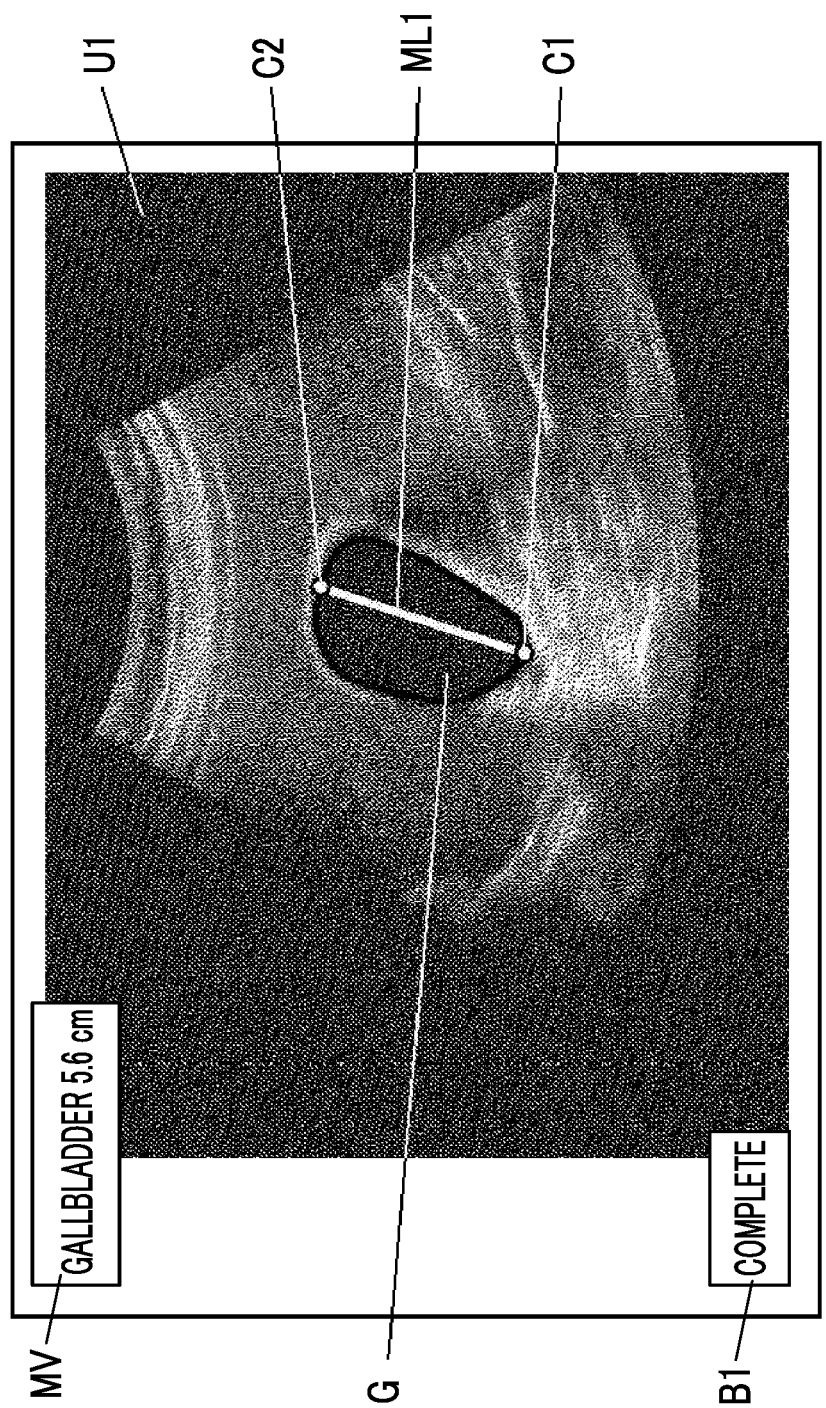
FIG. 6 is a diagram illustrating a display example of a measurement result.

In subsequent step S4, the measurement unit 8 disposes the caliper for measuring the measurement target detected in step S3 on the ultrasound image, and measures the measurement target using the disposed caliper. In this case, the measurement unit 8 measures the measurement target on the basis of the rule determined according to the measurement item by the detection and measurement algorithm. For example, in a case where the measurement item is the gallbladder size, as illustrated in FIG. 6, the measurement unit 8 measures the length of a measurement line ML1 having two calipers C1 and C2 disposed on the inner wall of the region representing a gallbladder G as the end points.

In step S5, the measurement unit 8 causes the display unit 7 to display the measurement result such as the caliper obtained in step S4. For example, as illustrated in FIG. 6, the measurement unit 8 can display the calipers C1 and C2, the measurement line ML1, a measurement value MV together with an ultrasound image U1 as the measurement result.

In subsequent step S6, it is determined whether there is a modification request for the position of the caliper disposed on the ultrasound image. For example, as illustrated in FIG. 6, a completion button B1 for completing the measurement of the measurement target is displayed together with the ultrasound image U1, and in a case where the completion button B1 is pressed by the user through the operation unit 16, it is determined that there is no modification request for the position of the calipers C1 and C2. In this case, the operation of the ultrasound diagnostic apparatus 1 is ended.

In step S6, in a case where it is determined that there is a modification request for the position of the caliper, the processing proceeds to step S7. For example, in a case where the user starts to change the position of the caliper C1 or C2 through the operation unit 16 without pressing the completion button B1 illustrated in FIG. 6, it is determined that there is a modification request for the measurement point.

In step S7, the contour detection unit 10 performs the image analysis on the ultrasound image acquired in step S1 to detect the contour of the measurement target detected by the measurement unit 8. In this case, for example, the contour detection unit 10 sets a detection region including the measurement target detected in step S3, and performs the image analysis on the ultrasound image in the detection region to detect the contour of the measurement target. In this manner, the contour detection unit 10 detects the inner wall of the gallbladder G as a contour E1 of the gallbladder G illustrated in FIG. 7, for example.

Figure 7:
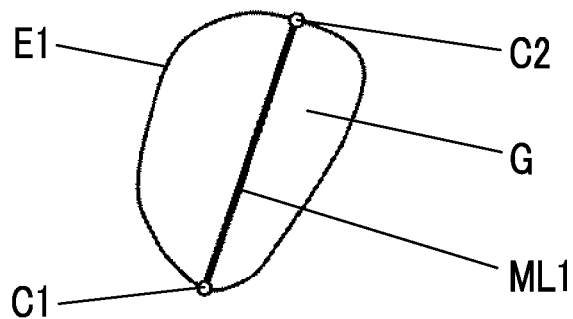
FIG. 7 is a diagram illustrating an example of a movable range of a caliper.

In step S8, the caliper movable range limit unit 11 limits the movable range of the caliper disposed on the ultrasound image in step S4 on the contour detected in step S7. For example, in a case where the measurement item is the gallbladder size, as illustrated in FIG. 7, the caliper movable range limit unit 11 limits the movable range of the calipers C1 and C2 on the contour E1 of the region illustrating the gallbladder G on the ultrasound image.

In step S9, in a case where the position of the caliper is modified by the user through the operation unit 16, the modification acceptance unit 15 accepts the modification of the caliper by the user. For example, in the example illustrated in FIG. 6, in a case where the completion button B1 is pressed after the position of the caliper C1 or C2 is changed by the user through the operation unit 16, the modification acceptance unit 15 determines that the modification of the caliper C1 or C2 is completed to accept the modification of the caliper C1 or C2 by the user.

Figure 8:
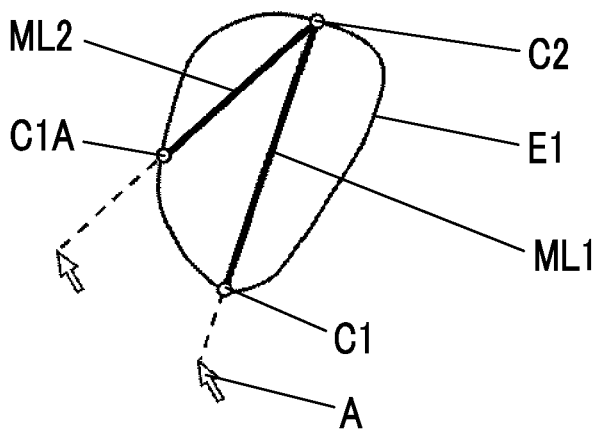
FIG. 8 is a diagram illustrating a modifying example of the caliper.

In addition, the user can modify the position of the caliper by dragging the caliper through the operation unit 16. For example, as illustrated in FIG. 8, the user operates a cursor A through the operation unit 16 so that the caliper C1 which is closer to the cursor A between the calipers C1 and C2 is dragged and moved. In this case, since the movable range of the caliper C1 is limited on the contour E1 of the measurement target, the caliper C1 is moved to an intersection between the contour E1 and a line segment connecting the caliper C2 which is not dragged by the cursor A to a point where the cursor A is dragged.

In a case where the cursor A drags the caliper C1 or C2, the movable range of the cursor A is limited on the contour E1 of the measurement target so that the caliper C1 or C2 can be set to be moved on the contour E1. In addition, in a case where the operation unit 16 is configured by the touch panel, as illustrated in FIG. 5, the caliper C1 or C2 may be touched and dragged by a finger F of the user instead of the cursor A so that the caliper C1 or C2 may be moved.

In subsequent step S10, the measurement unit 8 measures the measurement target on the basis of the caliper modified in step S9. For example, in a case where the position of the caliper C1 is modified to the position of a caliper C1A so that the measurement line ML1 is modified to a measurement line ML2 in step S9 as illustrated in FIG. 8, the measurement unit 8 measures the length of the new measurement line ML2.

In step S11, the measurement unit 8 causes the display unit 7 to display the measurement result such as the caliper modified in step S9 and the measurement value obtained in step S10. Thereby, the operation of the ultrasound diagnostic apparatus 1 is ended.

As described above, with the ultrasound diagnostic apparatus 1 of Embodiment 1 of the invention, in a case where the caliper automatically set by the measurement unit 8 in step S4 is modified by the user through the operation unit 16, since the movable range of the caliper is limited on the contour of the measurement target, it is possible for the user to easily and accurately modify manually the automatically set position of the caliper such that the caliper is disposed at an appropriate position for measuring the measurement target.

Modification Example 1

In Embodiment 1, an example in which the caliper C1 between the calipers C1 and C2 is dragged by the cursor A so that the position of the caliper C1 is modified is described, but the method of modifying the caliper is not limited thereto.

Figure 9:
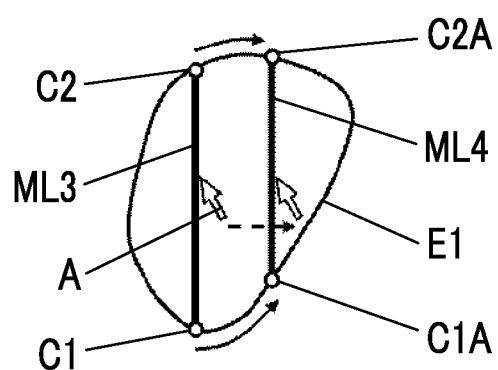
FIG. 9 is a diagram illustrating a modifying example of a caliper in Modification Example 1 of Embodiment 1 of the invention.

For example, as illustrated in FIG. 9, the positions of the calipers C1 and C2 can be moved by moving a measurement line ML3 using the cursor A while maintaining the tilt of the measurement line ML3 in a certain direction. In this case, following the movement of the measurement line ML3, the calipers C1 and C2 are moved on the contour E1 of the measurement target so as to form a measurement line along the same direction as the measurement line ML3. In the example illustrated in FIG. 9, the positions of the calipers C1 and C2 are respectively modified to positions of calipers C1A and C2A so that the measurement line ML3 is modified to a measurement line ML4.

Thereby, for example, in a case where the measurement result of the measurement target generally recommended to be measured using a measurement line extending along a certain direction is modified by a manual operation through the operation unit 16, it is possible for the user to easily and accurately perform the modification.

Modification Example 2

Figure 10:
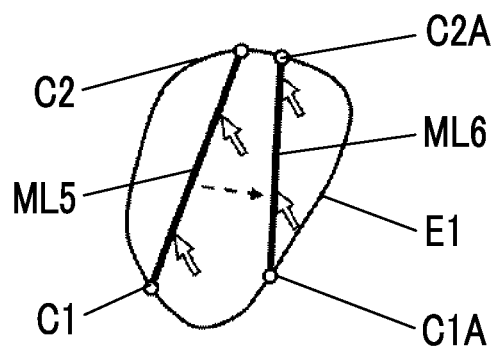
FIG. 10 is a diagram illustrating a modifying example of a caliper in Modification Example 2 of Embodiment 1 of the invention.

For example, in a case where the operation unit 16 is configured by the touch panel, as illustrated in FIG. 10, two points in the region representing the measurement target on the ultrasound image are dragged while being tapped by the finger F or the like of the user so that the calipers C1 and C2 can be moved to form a measurement line passing through the two points tapped by the user. In the example illustrated in FIG. 10, two points on a measurement line ML5 are dragged while being tapped by the user so that the calipers C1 and C2 are moved on the contour E1 of the measurement target to be modified to the calipers C1A and C2A, and thereby a new measurement line ML6 is obtained.

Thereby, it is possible for the user to modify the calipers C1 and C2 more intuitively and easily.

Modification Example 3

Further, the caliper movable range limit unit 11 can calculate a recommendation degree for the modification of the position of the caliper in each point on the contour E1 of the measurement target, and can change a display method of the measurement line connected to the caliper according to the calculated recommendation degree. Here, as the recommendation degree in each point on the contour E1 of the measurement target, for example, an index representing the edge likelihood of the ultrasound image on the contour E1 can be used. In this case, the recommendation degree can be calculated by the image analysis using the contrast between a point as the target on the ultrasound image and a surrounding point or the like. For example, as the recommendation degree, a value calculated according to the difference between the length of the measurement line connected to the caliper and the maximum diameter of the contour E1 can be used. In addition, for example, as the recommendation degree, a value calculated according to an angle difference between the measurement line connected to the caliper and the principal axis of inertia of the measurement target can be used.

Figure 11:
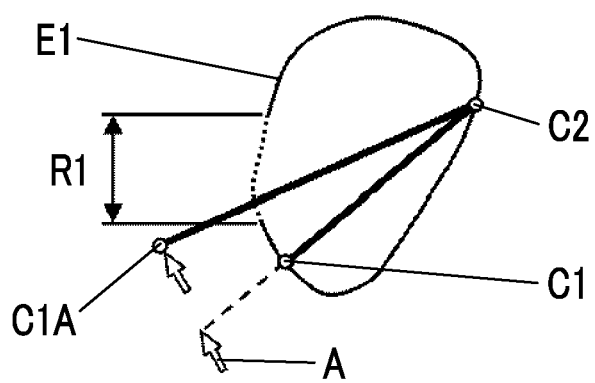
FIG. 11 is a diagram illustrating a modifying example of a caliper in Modification Example 3 of Embodiment 1 of the invention.

In this case, for example, as illustrated in FIG. 11, the caliper movable range limit unit 11 can cancel limiting the movable range of the calipers C1 and C2 on the contour E1, in a range R1 in which the calculated recommendation degree is lower than a predetermined reference value. For example, as illustrated in FIG. 11, in a case where the caliper C1 is dragged by the cursor A, the caliper C1 is moved on the contour E1, but the caliper C1 can be freely moved only within the range R1 in which the recommendation degree is lower than the predetermined reference value. In the example illustrated in FIG. 11, the caliper C1 is dragged into the range R1 to be moved to the position of the caliper CIA.

Since the user modifies the calipers C1 and C2 on the contour E1 of the measurement target while grasping the position with the recommendation degree greater than a certain value, it is possible to more accurately and easily modify the calipers C1 and C2.

Modification Example 4

Figure 12:
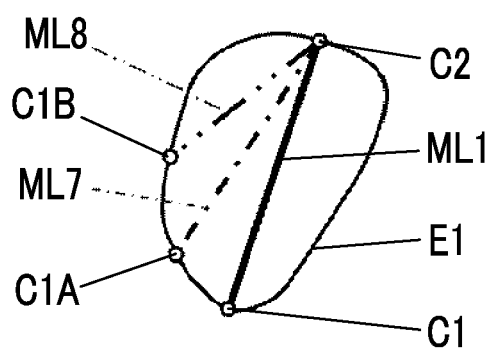
FIG. 12 is a diagram illustrating a display example of a modified caliper in Modification Example 4 of Embodiment 1 of the invention.

Further, as illustrated in FIG. 12, the caliper movable range limit unit 11 can change at least one of the color, thickness, or type of the measurement line connecting the calipers C1 and C2 according to the recommendation degree of the position on the contour E1 of the measurement target. In the example illustrated in FIG. 12, the caliper C1 is modified to the position of the caliper C1A so that the measurement line ML1 is modified to a measurement line ML7, the caliper C1 is modified to a position of a caliper C1B so that the measurement line ML1 is modified to a measurement line ML8, and these measurement lines ML1, ML7, and ML8 have different display aspects such as the color, thickness, and type according to the recommendation degree of the position on the contour E1.

Figure 13:
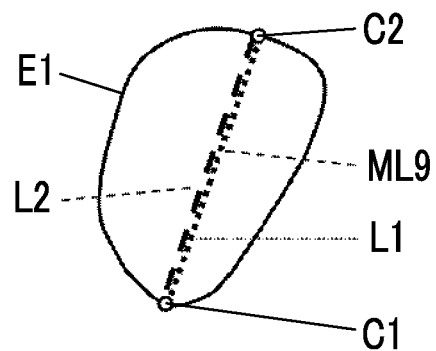
FIG. 13 is a diagram illustrating another display example of the modified caliper in Modification Example 4 of Embodiment 1 of the invention.

The caliper movable range limit unit 11 calculates a plurality of types of recommendation degrees calculated by a plurality of calculation methods, and can form the measurement line by using a plurality of lines having display aspects corresponding to the plurality of types of recommendation degrees. For example, as illustrated in FIG. 13, the caliper movable range limit unit 11 can form a measurement line ML9 by using line segments L1 and L2 having different display aspects such as the color, thickness, and type according to two types of recommendation degrees.

Thus, it is possible for the user to easily grasp the recommendation degree of the position on the contour E1 by changing the display aspect of the measurement line according to the recommendation degree of the position on the contour E1.

Modification Example 5

Figure 14:
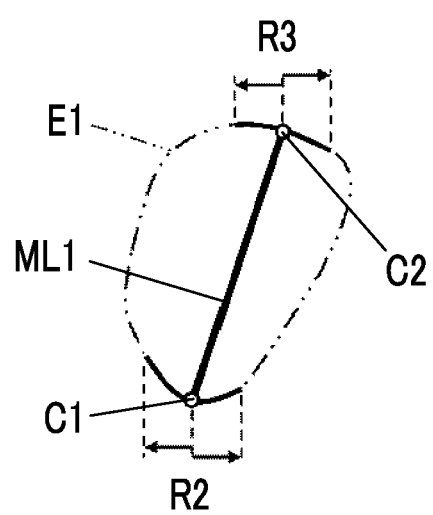
FIG. 14 is a diagram illustrating a modifying example of a caliper in Modification Example 5 of Embodiment 1 of the invention.

In addition, the caliper movable range limit unit 11 can learn the modification of the position of the caliper by the user through the operation unit 16, and further limit the movable range of the caliper to a portion on the contour E1 of the measurement target on the basis of the learning result. For example, as illustrated in FIG. 14, the caliper movable range limit unit 11 learns the modification results of the calipers C1 and C2 by the user, further limits the movable range of the caliper C1 to a range R2 having a certain length to the left and right from the position of the caliper C1 set by the measurement unit 8, and further limits the movable range of the caliper C2 to a range R3 having a certain length to the left and right from the position of the caliper C2 set by the measurement unit 8.

Thereby, since the movable ranges of the calipers C1 and C2 are limited in accordance with the tendency of the position modified by the user, it is possible for the user to more easily modify the calipers C1 and C2.

Modification Example 6

In case of measuring a diameter of the measurement target using an ultrasound image in which the contour of the measurement target is a closed curve, depending on the user, there may be a case where the measurement line is disposed such that the diameter of the measurement target is maximized and a case where the measurement line is disposed along the principal axis of inertia of the measurement target. Thus, for the measurement target for which there are a plurality of measurement rules depending on the user, it is possible to set the measurement rule for the next time according to the modification result of the user.

Figure 15:
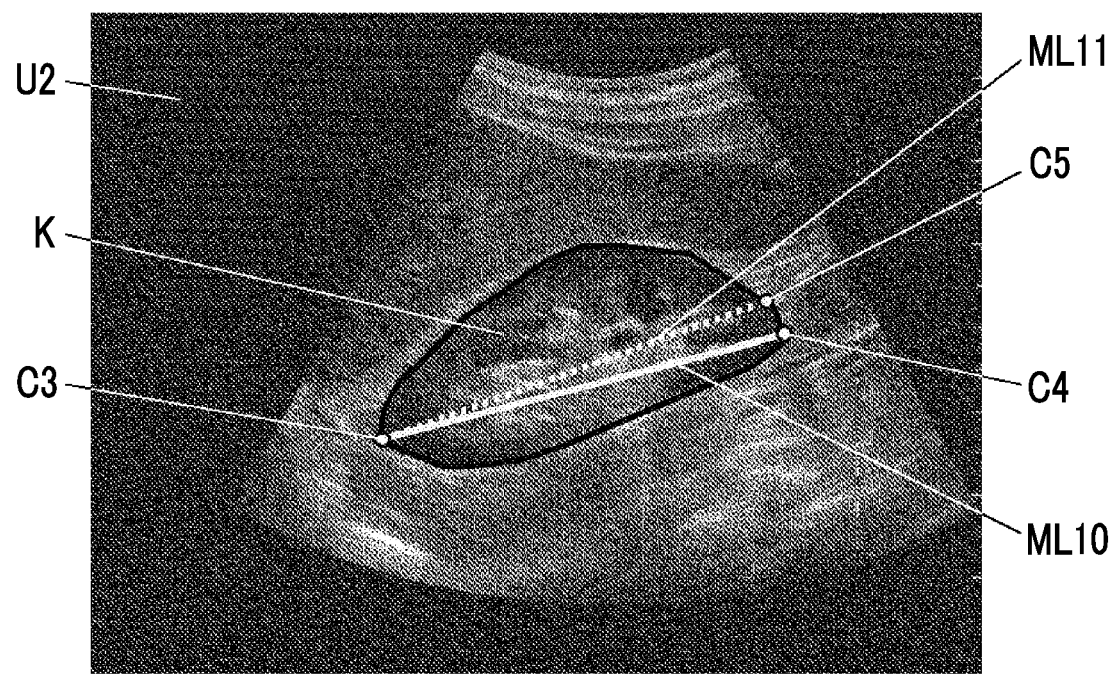
FIG. 15 is a diagram illustrating a disposition example of a caliper in Modification Example 6 of Embodiment 1 of the invention.

For example, as illustrated in FIG. 15, the measurement unit 8 calculates the measurement value for each of a measurement line ML10 in which the inner diameter of a kidney K is maximized and a measurement line ML11 along the principal axis of inertia of the kidney K, and causes the display unit 7 to display one of the two measurement lines ML10 and ML11. In this case, in a case where a caliper C3 or C4 as the end point of the measurement line ML10 or a caliper C3 or C5 as the end point of the measurement line ML11 is modified by the user through the operation unit 16, the detection and measurement algorithm setting unit 9 determines which of the measurement lines ML10 and ML11 the measurement line newly set by the modification of the caliper C3, C4 or C5 by the user is close to. Further, in a case where the measurement line newly set by the modification of the caliper C3, C4, or C5 is close to the measurement line ML10, the detection and measurement algorithm setting unit 9 sets a measurement line in which the inner diameter of the kidney K is maximized from the next measurement, and in a case where the new measurement line is close to the measurement line ML11, the detection and measurement algorithm setting unit 9 sets a measurement line along the principal axis of inertia of the kidney K from the next measurement.

Thus, by setting a measurement rule for the measurement target according to the modification result of the user, it is possible to perform measurement in accordance with the measurement rule used by the user from the next measurement.

Modification Example 7

Figure 16:
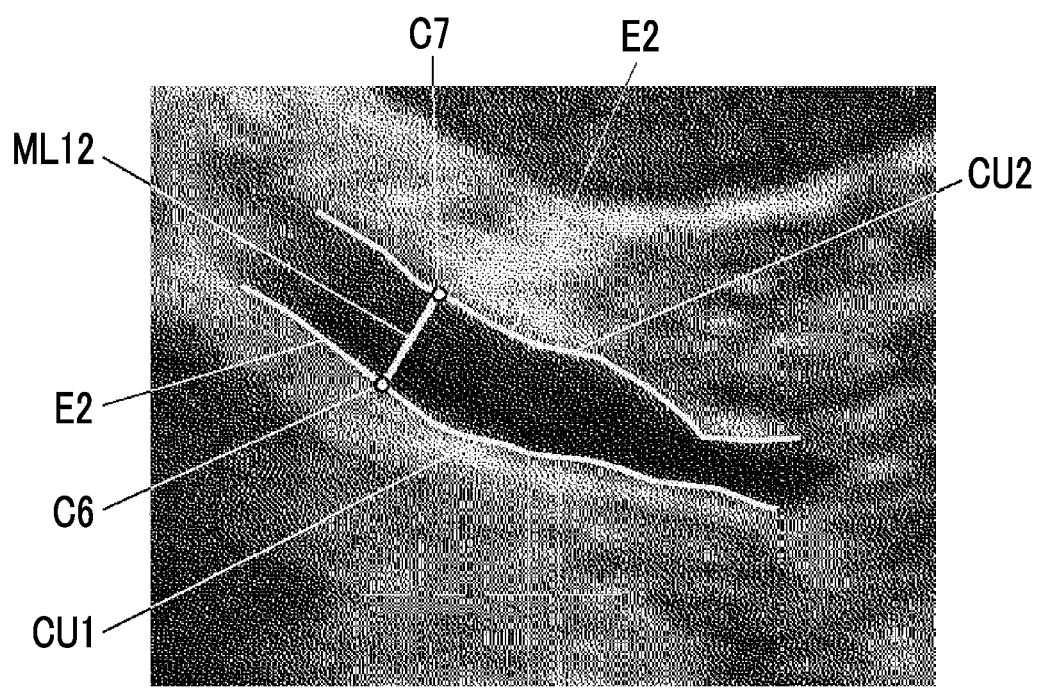
FIG. 16 is a diagram illustrating an example of a movable range of a caliper in Modification Example 7 of Embodiment 1 of the invention.

In Embodiment 1, an example in which the contour of the measurement target is constituted by a closed curve is described, but even in a case where the contour of the measurement target is constituted by a plurality of curves not by a closed curve, the invention can be applied. For example, in a case where the measurement target is a diameter of a site having a tubular structure such as a diameter of the inferior vena cava and a diameter of the common bile duct, as illustrated in FIG. 16, a contour E2 of the measurement target is constituted by two curves CU1 and CU2, and a measurement line ML12 having a caliper C6 disposed on the curve CU1 and a caliper C7 disposed on the curve CU2 as the end points is disposed.

Figure 17:
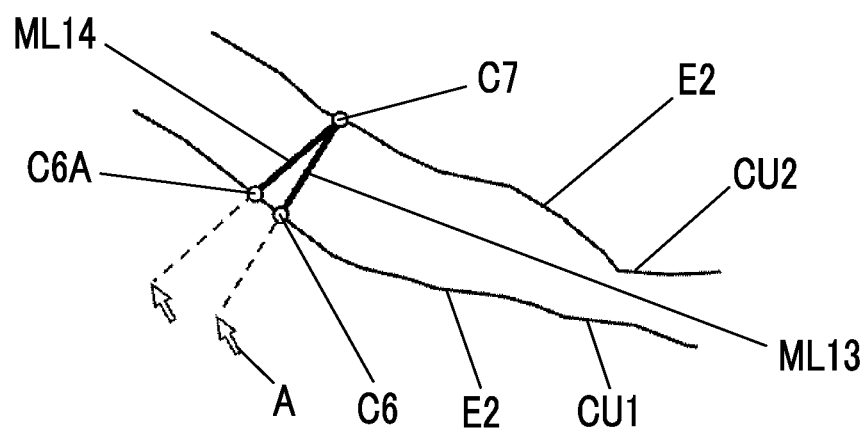
FIG. 17 is a diagram illustrating a modifying example of the caliper in Modification Example 7 of Embodiment 1 of the invention.

In such a case, the caliper movable range limit unit 11 can limit the movable range of the caliper C6 to the curve CU1, and limit the movable range of the caliper C7 to the curve CU2. For example, as illustrated in FIG. 17, the user operates the cursor A through the operation unit 16 so that the caliper C6 which is closer to the cursor A between the calipers C6 and C7 is dragged and moved. In this case, since the movable range of the caliper C6 is limited to the curve CU1 constituting the contour E2 of the measurement target, the caliper C6 is moved to an intersection between the curve CU1 and a line segment connecting the caliper C7 which is not dragged by the cursor A to a point where the cursor A is dragged. In the example illustrated in FIG. 17, the position of the caliper C6 is modified to a position of a caliper C6A so that a measurement line ML13 is modified to a measurement line ML14.

Modification Example 8

In a case where the measurement target is a diameter of a site having a tubular structure such as a diameter of the inferior vena cava and a diameter of the common bile duct, and the contour of the measurement target is constituted by a plurality of curves not a closed curve, the caliper movable range limit unit 11 can calculate an approximate straight line of the edge of the measurement target around the caliper, and limit the movable range of the caliper such that the measurement line connected to the caliper is moved while facing a direction perpendicular to the approximate straight line.

Figure 18:
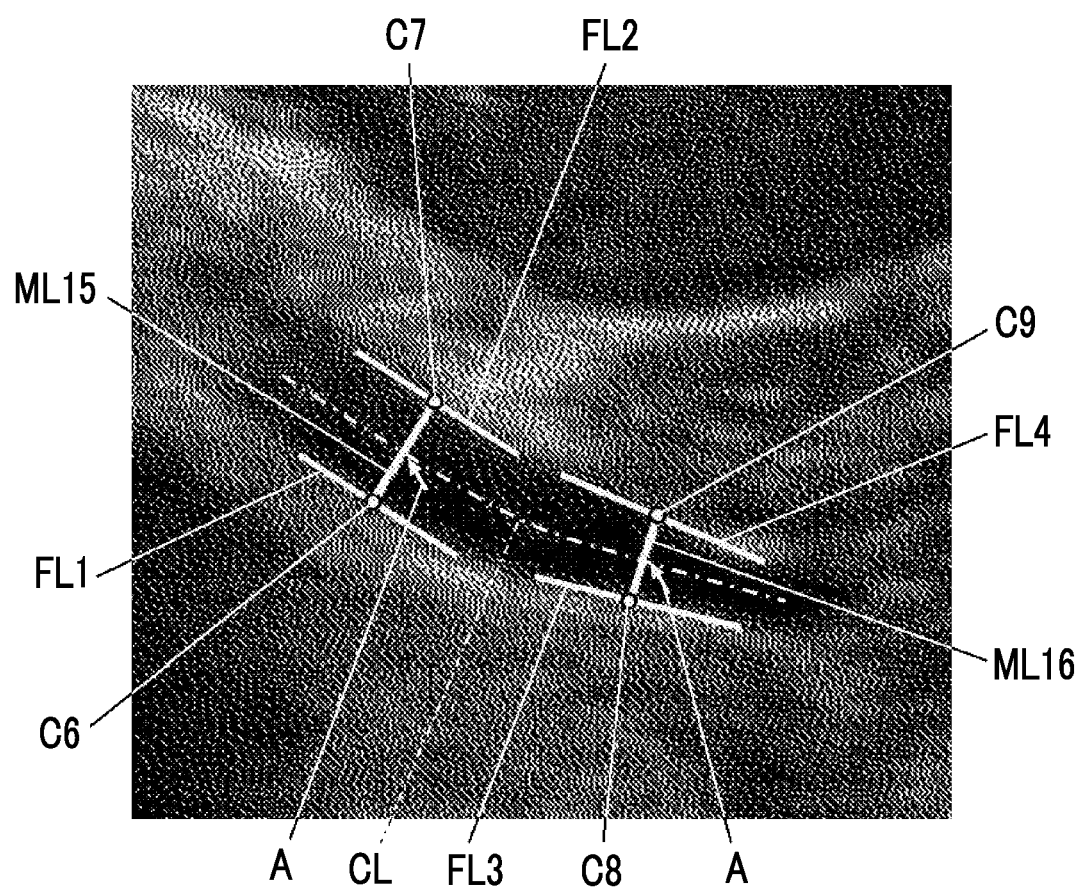
FIG. 18 is a diagram illustrating an example of a movable range of a caliper in Modification Example 8 of Embodiment 1 of the invention.

For example, as illustrated in FIG. 18, the caliper movable range limit unit 11 calculates two parallel approximate straight lines FL1 and FL2 of the edges of the measurement target which are respectively around two calipers C6 and C7 positioned on both ends of a measurement line ML15 on the basis of the contour of the measurement target detected by the contour detection unit 10, and limits the movable ranges of the calipers C6 and C7 to the approximate straight lines FL1 and FL2, respectively. In this case, the measurement line ML15 is dragged by the cursor A and is moved while facing a direction perpendicular to the approximate straight lines FL1 and FL2, that is, while being substantially orthogonal to a center line CL of the measurement target. In addition, the calipers C6 and C7 are moved following the measurement line ML15.

Further, for example, as illustrated in FIG. 18, the caliper movable range limit unit 11 can calculate two approximate straight lines FL3 and FL4 which are inclined at different angles, as the movable ranges of calipers C8 and C9. In this case, a measurement line ML16 having the calipers C8 and C9 disposed on the approximate straight lines FL3 and FL4 as the end points is dragged by the cursor A, and is moved while facing a direction perpendicular to an average angle of the approximate straight lines FL3 and FL4, that is, while being substantially orthogonal to the center line CL of the measurement target. In addition, the calipers C8 and C9 are moved following the measurement line ML16.

In this manner, it is possible for the user more easily modify the positions of the calipers C6 to C9 by limiting the movable ranges of the calipers C6 to C9.

In Embodiment 1, the caliper is disposed on the ultrasound image by the measurement unit 8 and then the contour of the measurement target is detected by the contour detection unit 10, but the contour of the measurement target may be detected and then the caliper may be disposed on the ultrasound image on the basis of the detected contour. For example, by providing the contour detection unit 10 to the measurement unit 8, in case of detecting the measurement target in step S3, the measurement unit 8 can detect the contour of the measurement target and dispose the caliper on the detected contour. For example, in a case where the measurement target is the gallbladder G, as illustrated in FIG. 7, the measurement unit 8 can detect the inner wall of the gallbladder G as the contour E1 of the gallbladder G, and dispose the calipers C1 and C2 on the contour E1.

Thus, in case of detecting the measurement target in step S3, in a case where the contour of the measurement target is detected, the movable range of the caliper is limited on the contour of the measurement target which is detected in step S3, by the caliper movable range limit unit 11 in step S8.

Embodiment 2

Figure 19:
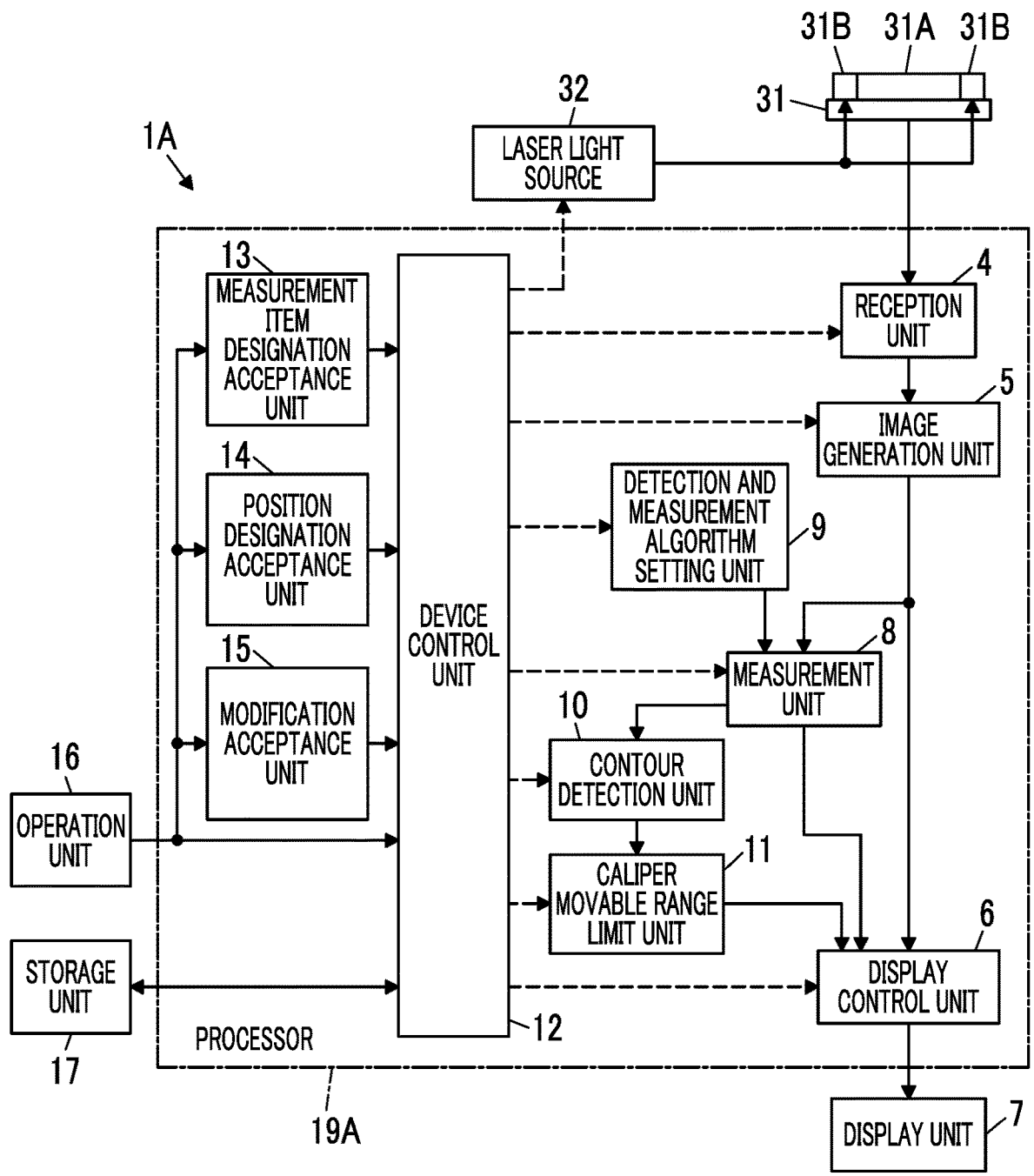
FIG. 19 is a block diagram illustrating a configuration of a photoacoustic wave diagnostic apparatus according to Embodiment 2 of the invention.

In Embodiment 1, the ultrasound diagnostic apparatus is described, but the invention can be applied to an acoustic wave diagnostic apparatus other than the ultrasound diagnostic apparatus, such as a photoacoustic wave diagnostic apparatus. FIG. 19 illustrates a configuration of a photoacoustic wave diagnostic apparatus 1A according to Embodiment 2. The photoacoustic wave diagnostic apparatus 1A is obtained such that the ultrasound diagnostic apparatus 1 of Embodiment 1 illustrated in FIG. 1 comprises a probe 31 instead of the probe 18 and comprises a laser light source 32 instead of the transmission unit 3.

The probe 31 has an array transducer 31A similar to the array transducer 2 of the ultrasound diagnostic apparatus 1 illustrated in FIG. 1 and a pair of laser light irradiation units 31B disposed on both end portions of the array transducer 31A. The array transducer 31A is connected to the reception unit 4. In addition, the pair of laser light irradiation units 31B is connected to the laser light source 32, and the laser light source 32 is connected to the device control unit 12.

In addition, the reception unit 4, the image generation unit 5, the display control unit 6, the measurement unit 8, the detection and measurement algorithm setting unit 9, the contour detection unit 10, the caliper movable range limit unit 11, the device control unit 12, the measurement item designation acceptance unit 13, the position designation acceptance unit 14, and the modification acceptance unit 15 constitute a processor 19A.

Figure 20:
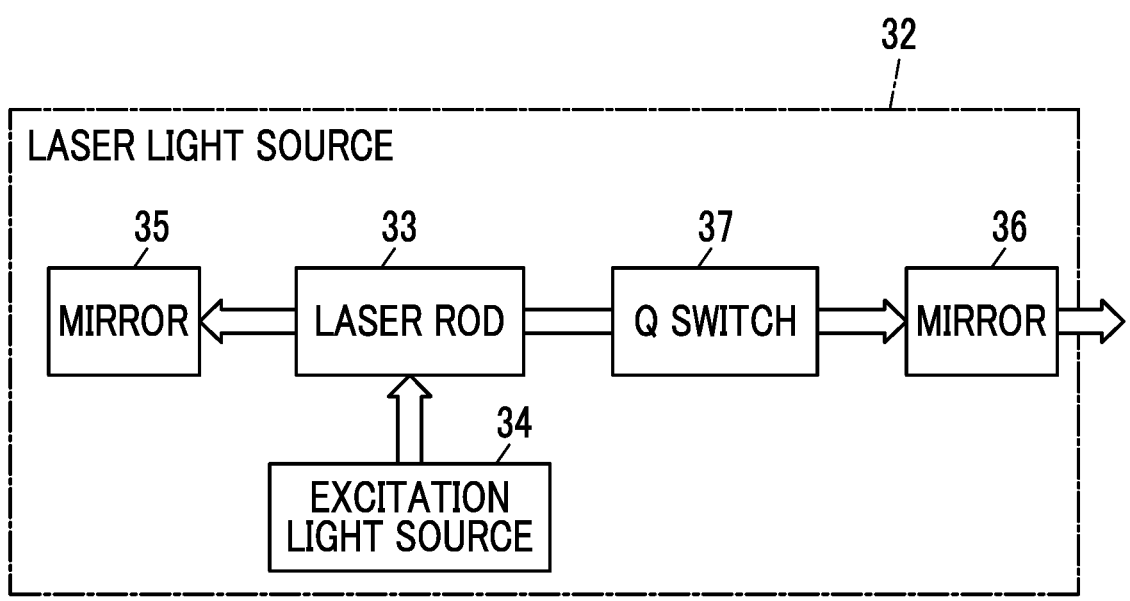
FIG. 20 is a block diagram illustrating an internal configuration of a laser light source in Embodiment 2 of the invention.

The laser light source 32 of the photoacoustic wave diagnostic apparatus 1A emits pulsed laser light under the control of the device control unit 12. As illustrated in FIG. 20, the laser light source 32 has a laser rod 33, an excitation light source 34, a mirror 35, a mirror 36, and a Q switch 37. The laser rod 33 is a laser medium, and for example, an alexandrite crystal, an Nd:YAG crystal, or the like can be used for the laser rod 33. The excitation light source 34 is a light source irradiating the laser rod 33 with excitation light, and for example, a light source such as a flash lamp and a laser diode can be used for the excitation light source 34.

The mirrors 35 and 36 face each other with the laser rod 33 interposed therebetween, the mirrors 35 and 36 constitute an optical resonator. In the optical resonator, the mirror 36 is the output side. In the optical resonator, the Q switch 37 is inserted, and a state in which the insertion loss in the optical resonator is large is rapidly changed to a state in which the insertion loss is small by the Q switch 37, thereby obtaining pulsed laser light. The pulsed laser light emitted from the mirror 36 on the output side of the laser light source 32 is guided to the laser light irradiation units 31B of the probe 31 through a light guide member (not illustrated) or the like.

The laser light irradiation units 31B of the probe 31 are disposed on the both ends of the array transducer 31A, and comes into contact with the body surface of the subject to emit the pulsed laser light, which is guided from the laser light source 32 through the light guide member (not illustrated) or the like, to the inside of the subject. The pulsed laser light emitted to the inside of the subject in this manner is absorbed as heat energy by an in-vivo substance such as hemoglobin contained in the subject, and the in-vivo substance that has absorbed the pulsed laser light expands and contracts to generate a photoacoustic wave.

The array transducer 31A of the probe 31 has the same configuration as the array transducer 2 illustrated in FIG. 1, but the array transducer 31A receives photoacoustic wave generated by the emission of the pulsed laser light from the laser light source 32 through the laser light irradiation units 31B to the inside of the subject, and outputs a photoacoustic wave reception signal to the reception unit 4. As in the reception signal based on the ultrasound echo in Embodiment 1, the photoacoustic wave reception signal obtained in this manner is sent to the image generation unit 5, and a photoacoustic image is generated by the image generation unit 5. The photoacoustic image generated in this manner is displayed on the display unit 7 through the display control unit 6, and is sent to the measurement unit 8 to be used in the measurement of the measurement target.

The contour detection unit 10 performs an image analysis on the photoacoustic image, and detects the contour of the measurement target detected by the measurement unit 8.

In the photoacoustic image, in a case where the caliper set by the measurement unit 8 is modified by the user through the operation unit 16, the caliper movable range limit unit 11 limits the movable range of the caliper on the contour of the measurement target detected by the contour detection unit 10. In a case where the caliper of which the movable range is limited in this manner is moved to be modified by the user through the operation unit 16, the measurement unit 8 measures the measurement target on the basis of the modified caliper, and causes the display unit 7 to display the measurement result.

As described above, the invention is also applied to the acoustic wave diagnostic apparatus such as the photoacoustic wave diagnostic apparatus 1A.

EXPLANATION OF REFERENCES

1: ultrasound diagnostic apparatus
2, 31A: array transducer
3: transmission unit
4: reception unit 5: image generation unit
6: display control unit
7: display unit
8: measurement unit
9: detection and measurement algorithm setting unit
10: contour detection unit
11: caliper movable range limit unit
12: device control unit
13: measurement item designation acceptance unit
14: position designation acceptance unit
15: modification acceptance unit
16: operation unit
17: storage unit
18, 31: probe
19: processor
20: amplification unit
21: AD conversion unit
22: signal processing unit
23: DSC
24: image processing unit
31B: laser light irradiation unit
32: laser light source
33: laser rod
34: excitation light source
35, 36: mirror
37: Q switch
A: cursor
B1: completion button
C1, C1A, C1B, C2, C2A, C3, C4, C5, C6, C6A, C7, C8, C9: caliper
CL: center line
CU1, CU2: curve
E1, E2: contour
F: finger
FL3, FL4: approximate straight line
G: gallbladder
K: kidney
M: list
ML1, ML2, ML3, ML4, ML5, ML6, ML7, ML8, ML9, ML10, ML11, ML12, ML13, ML14, ML15, ML16: measurement line
MV: measurement value
R1, R2, R3: range
U1, U2: ultrasound image

What is claimed is:

1. An acoustic wave diagnostic apparatus comprising:
a display monitor configured to display an acquired acoustic wave image;
an operation device configured to perform an input operation by an user; and
a processor configured to
accept designation of a measurement item relating to a measurement target through the operation device,
set a detection and measurement algorithm on the basis of the accepted measurement item,
accept designation of a position of the measurement target on the acoustic wave image displayed on the display monitor, through the operation device,
detect the measurement target and set a caliper on the detected measurement target to perform measurement on the basis of the accepted position of the measurement target and the set detection and measurement algorithm,
display a measurement result on the display monitor,
once a modification of a position of the caliper is requested by the user through the operation device,
detect a contour of the measurement target on the acoustic wave image,
limit a movable range of the caliper to only along the contour which is detected, in the modification of the position of the caliper performed by the user through the operation device,
make the caliper move continuously only along the contour based on an input operation of the user via the operation device, in the modification of the position of the caliper performed by the user through the operation device,
accept the modification of the position of the caliper which is performed by the user through the operation device,
measure the measurement target on the basis of the accepted modification of the position of the caliper, and
causes the display monitor to display a measurement result.

2. The acoustic wave diagnostic apparatus according to claim 1, wherein
the processor is further configured to limit the movable range of the caliper such that a measurement line connected to the caliper is moved while facing a predetermined direction.

3. The acoustic wave diagnostic apparatus according to claim 1, wherein the processor is configured to
calculate an approximate straight line of an edge of the measurement target around the caliper, and
limit the movable range of the caliper such that a measurement line connected to the caliper is moved while facing a direction perpendicular to the approximate straight line.

4. The acoustic wave diagnostic apparatus according to claim 1, wherein
the caliper is composed of two calipers, and
the processor is further configured to
calculate two approximate straight lines of edges of the measurement target around the two calipers as the contour of the measurement target, and
limit the movable ranges of the two calipers such that a straight measurement line connecting between the two calipers is moved while facing a direction perpendicular to an average angle of the two approximate straight lines.

5. The acoustic wave diagnostic apparatus according to claim 1, wherein the processor is further configured to
calculate a recommendation degree for the modification of the position of the caliper in each point on the contour, and
change a display method of a measurement line connected to the caliper according to the calculated recommendation degree.

6. The acoustic wave diagnostic apparatus according to claim 2, wherein the processor is further configured to
calculate a recommendation degree for the modification of the position of the caliper in each point on the contour, and
change a display method of a measurement line connected to the caliper according to the calculated recommendation degree.

7. The acoustic wave diagnostic apparatus according to claim 3, wherein the processor is further configured to
calculate a recommendation degree for the modification of the position of the caliper in each point on the contour, and change a display method of a measurement line connected to the caliper according to the calculated recommendation degree.

8. The acoustic wave diagnostic apparatus according to claim 4, wherein the processor is further configured to
calculate a recommendation degree for the modification of the position of the two calipers in each point on the approximate straight lines, and
change a display method of a measurement line connected to the caliper according to the calculated recommendation degree.

9. The acoustic wave diagnostic apparatus according to claim 5, wherein the processor is further configured to
calculate the recommendation degree according to edge likelihood of the measurement target.

10. The acoustic wave diagnostic apparatus according to claim 6, wherein the processor is further configured to
calculate the recommendation degree according to edge likelihood of the measurement target.

11. The acoustic wave diagnostic apparatus according to claim 7, wherein the processor is further configured to
calculate the recommendation degree according to edge likelihood of the measurement target.

12. The acoustic wave diagnostic apparatus according to claim 5, wherein the processor is further configured to
calculate the recommendation degree according to a difference between a length of the measurement line connected to the caliper and a maximum diameter of the contour.

13. The acoustic wave diagnostic apparatus according to claim 6, wherein the processor is further configured to
calculate the recommendation degree according to a difference between a length of the measurement line connected to the caliper and a maximum diameter of the contour.

14. The acoustic wave diagnostic apparatus according to claim 5, wherein the processor is further configured to
calculate the recommendation degree according to an angle difference between the measurement line connected to the caliper and a principal axis of inertia of the measurement target.

15. The acoustic wave diagnostic apparatus according to claim 6, wherein the processor is further configured to
calculate the recommendation degree according to an angle difference between the measurement line connected to the caliper and a principal axis of inertia of the measurement target.

16. The acoustic wave diagnostic apparatus according to claim 9, wherein the processor is further configured to
change at least one of a color, thickness, or type of the measurement line according to the recommendation degree.

17. The acoustic wave diagnostic apparatus according to claim 5, wherein the processor is further configured to
cancel limiting the movable range of the caliper on the contour, at a position where the calculated recommendation degree is lower than a predetermined reference value.

18. The acoustic wave diagnostic apparatus according to claim 1, wherein the processor is further configured to
learn the modification of the position of the caliper by the user, and
further limit the movable range of the caliper to a portion on the contour on the basis of a learning result.

19. The acoustic wave diagnostic apparatus according to claim 1, wherein
the acoustic wave image is an ultrasound image or a photoacoustic image.

20. A control method of an acoustic wave diagnostic apparatus, the control method comprising:
displaying an acquired acoustic wave image;
accepting designation of a measurement item relating to a measurement target from a user;
setting a detection and measurement algorithm on the basis of the accepted measurement item;
accepting designation of a position of the measurement target on the displayed acoustic wave image from the user;
detecting the measurement target and setting a caliper on the detected measurement target to perform measurement on the basis of the accepted position of the measurement target and the set detection and measurement algorithm,
displaying a measurement result;
once a modification of a position of the caliper is requested by the user through an operation device,
detecting a contour of the measurement target on the acoustic wave image;
limiting a movable range of the caliper to only along the contour which is detected, in the modification of the position of the caliper performed by the user through the operation device;
making the caliper move continuously only along the contour based on an input operation of the user via the operation device, in the modification of the position of the caliper performed by the user through the operation device;
accepting the modification of the position of the caliper by the user through the operation device;
measuring the measurement target on the basis of the accepted modification of the position of the caliper; and
displaying a measurement result.

\* \* \* \* \*